United States Patent
Tatonetti et al.

(10) Patent No.: US 10,354,202 B2
(45) Date of Patent: Jul. 16, 2019

(54) SIGNAL DETECTION ALGORITHMS TO IDENTIFY DRUG EFFECTS AND DRUG INTERACTIONS

(71) Applicant: The Board of Trustees of the Leland Stanford Junior University, Stanford, CA (US)

(72) Inventors: Nicholas Tatonetti, New York, NY (US); Russ B. Altman, Menlo Park, CA (US); Guy Haskin Fernald, San Francisco, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 116 days.

(21) Appl. No.: 15/090,425

(22) Filed: Apr. 4, 2016

(65) Prior Publication Data

US 2016/0217395 A1    Jul. 28, 2016

Related U.S. Application Data

(63) Continuation of application No. 13/738,966, filed on Jan. 10, 2013, now Pat. No. 9,305,267.

(60) Provisional application No. 61/585,198, filed on Jan. 10, 2012.

(51) Int. Cl.
    *G06F 15/18*     (2006.01)
    *G06N 20/00*     (2019.01)
    *G16H 50/50*     (2018.01)
    *G06F 19/00*     (2018.01)

(52) U.S. Cl.
    CPC ............. *G06N 20/00* (2019.01); *G16H 50/50* (2018.01); *G06F 19/36* (2013.01)

(58) Field of Classification Search
    CPC .... G06F 19/3437; G06F 19/36; G06N 99/005
    See application file for complete search history.

(56) References Cited

U.S. PATENT DOCUMENTS

| 9,305,267 B2 | 4/2016 | Tatonetti et al. | |
| 2003/0182136 A1* | 9/2003 | Horton | G06Q 30/02 706/45 |
| 2007/0128597 A1* | 6/2007 | Schwers | C12Q 1/6883 435/6.11 |
| 2009/0043752 A1* | 2/2009 | Kenedy | G06F 19/345 707/999.005 |

(Continued)

OTHER PUBLICATIONS

"A Bayesian neural network method for adverse drug reaction signal generation"; Bate et al Eur J Clin Pharmacol (1998) 54: 315-321 (c) Springer-Verlag 1998.*

(Continued)

*Primary Examiner* — Luis A Sitiriche
(74) *Attorney, Agent, or Firm* — KPPB LLP

(57) ABSTRACT

An algorithm according to an embodiment of the present invention provides for latent signal detection of adverse events. Embodiments infer the presence of adverse drug events from large observational databases housed by the FDA, WHO, and other governmental organizations. The disclosed algorithms do not require the adverse event to be reported explicitly. Instead, the algorithms infer the presence of adverse events through more common secondary effects. In an embodiment, machine learning techniques are used for this purpose.

20 Claims, 4 Drawing Sheets

(56) References Cited

U.S. PATENT DOCUMENTS

| | | | | |
|---|---|---|---|---|
| 2009/0043795 | A1* | 2/2009 | Kenedy | G06F 19/345 |
| | | | | 707/999.101 |
| 2009/0259685 | A1* | 10/2009 | Agrawal | G06Q 30/02 |
| | | | | 707/999.107 |
| 2010/0046378 | A1* | 2/2010 | Knapp | H04L 12/2602 |
| | | | | 370/242 |
| 2013/0144636 | A1* | 6/2013 | Pouliot | G06F 19/326 |
| | | | | 705/2 |
| 2013/0179138 | A1* | 7/2013 | Jackson | G06F 19/18 |
| | | | | 703/11 |

OTHER PUBLICATIONS

"A Data Mining Approach for Signal Detection and Analysis"; Bate et al Drug safety 2002 (c) Adis International Limited.*

"The Use of a Bayesian Confidence Propagation Neural Network in Pharmacovigilance"; Andrew Bate Division of Clinical Pharmacology Department of Pharmacology and Clinical Neuroscience, Umeå University 2003.*

"Predicting drug side-effect profiles: a chemical fragment-based approach"; Pauwels et al Pauwels et al. BMC Bioinformatics 2011, 12:169 http://www.biomedcentral.com/1471-2105/12/169.*

"Gaining Insight into Off-Target Mediated Effects of Drug Candidates with a Comprehensive Systems Chemical Biology Analysis"; Scheiber et al; J. Chem. Inf. Model., Article ASAP o DOI: 10.1021/ci800344p Downloaded from http://pubs.acs.org on Jan. 28, 2009.*

"A side effect resource to capture phenotypic effects of drugs"; Kuhn et al Molecular Systems Biology 6; Article No. 343; doi:10.1038/msb.2009.98 Citation: Molecular Systems Biology 6:343 & 2010 EMBO and Macmillan Publishers Limited All rights reserved 1744-4292/10 Published online: Jan. 19, 2010.*

"Analysis of Pharmacology Data and the Prediction of Adverse Drug Reactions and Off-Target Effects from Chemical Structure"; Bender et al; ChemMedChem 2007, 2, 861-873 (c) 2007 Wiley-VCH Verlag GmbH& Co. KGaA, Weinheim.*

"Predicting and Preventing Adverse Drug Reactions in the Very Old"; Merle et al (c) 2005 Adis Data Information BV. All rights reserved.*

"Predicting adverse side effects of drugs"; Huang et al From BIOCOMP 2010. The 2010 International Conference on Bioinformatics and Computational Biology Las Vegas, NV, USA. Jul. 12-15, 2010.*

Adams et al., "A Mapping of Drug Space from the Viewpoint of Small Molecule Metabolism", PLoS Computational Biology, Aug. 2009, vol. 5, Issue 8, 12 pgs.

Ashburn et al., "Drug Repositioning: Identifying and Developing new Uses for Existing Drugs", Nature Reviews, Drug Discovery, Aug. 2004, vol. 3, pp. 673-683.

Bailey et al., "Grapefruit juice-drug interactions", Br. J. Clin. Pharmacol., 1998, vol. 46, pp. 101-110.

Campillos et al., "Drug Target Identification Using Side-Effect Similarity", Science, Jul. 11, 2008, vol. 321, pp. 263-266.

Dumouchel, "Bayesian Data Mining in Large Frequency Tables, With an Application to the FDA Spontaneous Reporting System", The American Statistician, Aug. 1999, vol. 53, No. 3, pp. 177-202.

Dumouchel et al., "Empirical Bayes Screening for Multi-Item Associations", Proceedings of the Seventh ACM SIGKDD International Conference on Knowledge Discovery and Data Mining, 2001, pp. 67-76.

El Olvey et al., "Comparison of Critical Drug-Drug Interaction Listings: The Department of Veterans Affairs Medical System and Standard Reference Compendia", Nature, Jan. 2010, vol. 87, No. 1, pp. 48-51.

Harpaz et al., "Mining multi-item drug adverse effect associations in spontaneous reporting systems", BMC Bioinformatics 2010, vol. 11, 8 pgs.

Hochberg et al., "Time-to-Signal Comparison for Drug Safety Data-Mining Algorithms vis. Traditional Signaling Criteria", Nature, Jun. 2009, vol. 85, No. 6, pp. 600-606.

Keiser et al., "Relating protein pharmacology by ligand chemistry", Nature Biotechnology, Feb. 2007, vol. 25, No. 2, pp. 197-206.

Kuhn et al., "STITCH: interaction networks of chemical and proteins", Nucleic Acids Research, 2008, vol. 36, Database issue, Published online Dec. 15, 2007, pp. D684-D688.

Mertens-Talcott et al., "Grapefruit-Drug Interactions: Can Interactions with Drugs be Avoided?", J. Clin. Pharmacol. 2006, vol. 46, pp. 1390-1416.

Neuvonen et al., "Drug interactions with lipid-lowering drugs: Mechanisms and clinical relevance", Clinical Pharmacology & Therapeutics, Dec. 2006, vol. 80, No. 6, pp. 565-581.

Noren et al., "A statistical methodology for drug-drug interaction surveillance", Statistics in Medicine, 2008, vol. 27, pp. 3057-3070.

Overington et al., "How many drug targets are there?", Nature Reviews, Drug Discovery, Dec. 2006, vol. 5, pp. 993-996.

Rawlins, "Spontaneous reporting of adverse drug reactions", Br. J. Clin. Pharmac., 1998, vol. 26, pp. 1-5.

Tatonetti et al., "Detecting Drug Interactions from Adverse-Vent Reports: Interaction Between Paroxetine and Pravastatin Increases Blood Glucose Levels", Clinical Pharmacology & Therapeutics, Jul. 2011, vol. 90, No. 1, pp. 133-142.

Tatonetti et al., "Predicting drug side-effects by chemical systems biology", Genome Biology, 2009, vol. 10, pp. 238.1-238.4.

Van Der Heijden et al., "On the assessment of adverse drug reactions from spontaneous reporting systems: the influence of under-reporting on odds ratios", Statistics in Medicine, 2002, vol. 21, pp. 2027-2044.

Xi E et al., "Drug Discovery Using Chemical Systems Biology: Identification of the Protein-Ligand Binding Network to Explain the Side Effects of CETP Inhibitors", PLoS Computational Biology, May 2009, vol. 5, Issue 5, 12 pgs.

Yap et al., "Clinically relevant drug interactions between anticancer drugs and psychotropic agents", European Journal of Cancer Care, 2011, vol. 20, pp. 6-32.

"About MedEffect Canada", Government of Canada, https://www.canada.ca/en/health-canada/services/drugs-health-products/medeffect-canada/medeffect-canada.html, 3 pgs.

"Adverse Event Reporting System (AERS)", U.S. Food and Drug Administration, Jan. 5, 2012, retrieved from https://web.archive.org/web/20120105161210/https://www.fda.gov/Drugs/GuidanceComplianceRegulatoryInformation/Surveillance/AdverseDrugEffects/default.htm on May 14, 2018, 3 pgs.

"SIDER Side Effect Resource", Side Effects, Dec. 9, 2011, retrieved from https://web.archive.org/web/20111209140424/http://sideeffects.embl.de/ on May 14, 2018, 1 page.

* cited by examiner

SIGNAL DETECTION ALGORITHMS TO IDENTIFY DRUG EFFECTS AND DRUG INTERACTIONS

CROSS-REFERENCE TO RELATED APPLICATIONS

The current application is a continuation of U.S. patent application Ser. No. 13/738,966 entitled "Signal Detection Algorithms to Identify Drug Effects and Drug Interactions" to Tatonetti et al., filed Jan. 10, 2013 which application claims priority under 35 U.S.C. § 119(e) to U.S. Provisional Application Ser. No. 61/585,198 entitled "Signal Detection Algorithms to Identify Drug Effects and Drug Interactions" to Tatonetti et al., filed Jan. 10, 2012. The disclosures of application Ser. Nos. 13/738,966 and 61/585,198 are hereby incorporated by reference in their entirety.

GOVERNMENT RIGHTS

This invention was made with Government support under contract GM061374 awarded by the National Institutes of Health. The Government has certain rights in this invention.

FIELD OF THE INVENTION

The present invention generally relates to the field of computer-aided diagnostics. More particularly, the present invention relates to a computer implemented method for determining adverse events associated with patients taking a drug or combination of drugs.

BACKGROUND OF THE INVENTION

Adverse drug events remain a leading cause of morbidity and mortality in the United States and around the world. In addition, nearly 30% of investigated drugs fail, clinical trials due to unexpected adverse events. Large collections of adverse drug event reports are maintained by the Food and Drug Administration and other organizations.

Currently, hypotheses about drug side effects are generated through quantitative signal detection. These methods compare the expected reporting frequencies between drugs and side effects to the actual frequencies. But uncharacterized biases in spontaneous reporting systems, such as prescription bias, patient demographic biases, concomitant drug use, and co-morbidities, significantly limit the effectiveness of these algorithms.

SUMMARY OF THE INVENTION

The databases maintained by the FDA and other organizations present an opportunity to study the full range of drug effects. In embodiments of the present invention, data-driven methods are implemented that correct for drug effects. Embodiments of the present invention provide significantly improved performance in at least two benchmark settings: associating drugs to their known side-effects using the FDA drug labels, and predicting future adverse event reporting patterns in two spontaneous reporting systems.

An algorithm according to an embodiment of the present invention provides for latent signal detection. Among other things, this algorithm infers the presence of adverse drug events from large observational databases housed by the FDA, WHO, and other governmental organizations. This algorithm does not require the adverse event to be reported explicitly. Instead, this algorithm infers its presence through more common secondary effects. In an embodiment, machine learning techniques are used for this purpose.

Another algorithm according to an embodiment of the present invention provides for statistical correction of uncharacterized bias. The same large database housed by governmental organizations can be biased, which makes analysis difficult and inference more difficult. Further, these biases are "uncorrectable" in that the covariates that may explain them may not be collected in the databases. These issues have severely limited the utility of traditional statistical methods when applied to these data.

A method according to an embodiment of the invention, however, uses covariances in drug co-prescription and co-morbidities to approximate these biases. Statistical methods are disclosed according to an embodiment of the present invention that outperform the traditional methods. It has been shown that a method according to an embodiment of the present invention can implicitly correct for the effect of a covariate that is not actually measured. This method is a type of automated cohort matching.

In an embodiment of the present invention, a database of off-label drug effects was developed. The methods according to embodiments of the present invention allowed for constructing of a database of high confidence off-label drug effects. Many of these drug effects are severe and may require future action by the FDA to include them on the drug label or investigate further for possible withdrawal or restriction of drug use. Others may be minor or rare and may not warrant significant further action. They are, however, useful in terms of understanding the pharmacology of small molecules.

In another embodiment of the present invention, a database of drug-to-drug interaction effects was developed. More particularly, a database of over 600,000 putative drug-drug interactions was constructed. This is drug interaction database also includes phenotypic effects of drugs whereas traditional data sources simply list that a drug interaction exists or that there is potential for an interaction and do not provide information on the type of interaction.

Applications of the methods and databases according to embodiments of the present invention include drug safety surveillance, computational drug discovery, predicting efficacy and safety of drugs in development, identification and inference of missing data in large databases, early detection of disease (e.g., cancers and chronic illnesses), evaluation and analysis of the Electronic Medical Records, evaluation and analysis of web search logs, and evaluation and analysis of any large observational data source with unknown biases (e.g. large scale high energy physics experiments).

These and other embodiments can be more fully appreciated upon an understanding of the detailed description of the invention as disclosed below in conjunction with the attached figures.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION OF THE INVENTION

Figure 1:
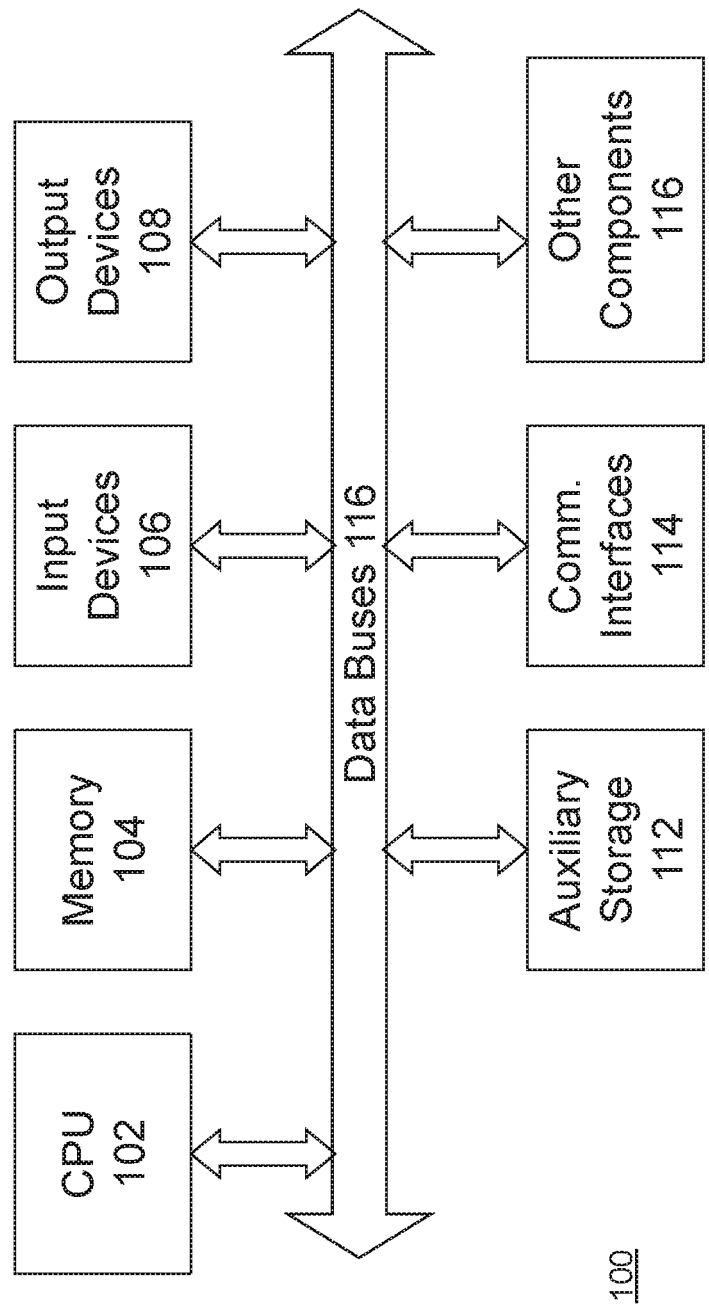
FIG. 1 is a block diagram of a computer system on which methods according to the present invention can be implemented.

Among other things, the present invention relates to methods, techniques, and algorithms that are intended to be implemented in a digital computer system 100 such as generally shown in FIG. 1. Such a digital computer is well-known in the art and may include the following.

Computer System

Computer system 100 may include at least one central processing unit 102 but may include many processors or processing cores. Computer system 100 may further include memory 104 in different forms such as RAM, ROM, hard disk, optical drives, and removable drives that may further include drive controllers and other hardware. Auxiliary storage 112 may also be include that can be similar to memory 104 but may be more remotely incorporated such as in a distributed computer system with distributed memory capabilities.

Computer system 100 may further include at least one output device 108 such as a display unit, video hardware, or other peripherals (e.g., printer). At least one input device 106 may also be included in computer system 100 that may include a pointing device (e.g., mouse), a text input device (e.g., keyboard), or touch screen.

Communications interfaces 114 also form an important aspect of computer system 100 especially where computer system 100 is deployed as a distributed computer system. Computer interfaces 114 may include LAN network adapters, WAN network adapters, wireless interfaces, Bluetooth interfaces, modems and other networking interfaces as currently available and as may be developed in the future.

Computer system 100 may further include other components 116 that may be generally available components as well as specially developed components for implementation of the present invention. Importantly, computer system 100 incorporates various data buses 116 that are intended to allow for communication of the various components of computer system 100. Data buses 116 include, for example, input/output buses and bus controllers.

Indeed, the present invention is not limited to computer system 100 as known at the time of the invention. Instead, the present invention is intended to be deployed in future computer systems with more advanced technology that can make use of all aspects of the present invention. It is expected that computer technology will continue to advance but one of ordinary skill in the art will be able to take the present disclosure and implement the described teachings on the more advanced computers or other digital devices such as mobile telephones or "smart" televisions as they become available. Moreover, the present invention may be implemented on one or more distributed computers. Still further, the present invention may be implemented in various types of software languages including C, C++, and others. Also, one of ordinary skill in the art is familiar with compiling software source code into executable software that may be stored in various forms and in various media (e.g., magnetic, optical, solid state, etc.). One of ordinary skill in the art is familiar with the use of computers and software languages and, with an understanding of the present disclosure, will be able to implement the present teachings for use on a wide variety of computers.

The present disclosure provides a detailed explanation of the present invention with detailed explanations that allow one of ordinary skill in the art to implement the present invention into a computerized method. Certain of these and other details are not included in the present disclosure so as not to detract from the teachings presented herein but it is understood that one of ordinary skill in the art would be familiar with such details.

Signal Detection Algorithms

Adverse drug events (ADEs) remain a significant source of mortality and morbidity around the world. In fact, ADEs account for 50,000 deaths each year. Many of these ADEs are unexpected since they are rare and not observed in relatively small clinical trials. To address this issue, large adverse event reporting systems have been created by the Food and Drug Administration, the World Health Organization, and Health Canada. These spontaneous reporting systems solicit volunteered adverse event reports from clinicians, patients, and pharmaceutical companies. The FDA's Adverse Event Reporting System (AERS) alone contains over three million adverse event reports collected over the last 30 years.

Quantitative signal detection algorithms use these data to flag and prioritize drug-event signals for follow up analysis and to discover complex relationships that are difficult to identify manually (e.g., drug-drug interactions). Well recognized biases in reporting, patient cohorts, and prescription limit the utility of these algorithms.

When applied to spontaneous adverse event reporting systems, signal detection algorithms attempt to quantify the "unexpectedness" of each drug-event association and flag drug-event pairs for follow up analysis. They do so by comparing the observed reporting rates between a drug-adverse event pair to the expected reporting rates for that pair. Under the null hypothesis, namely that the drug is not associated with the adverse event, the observed and expected values will be equivalent and their ratio equal to one.

The utility of these algorithms has been hampered by biases in the data that challenge their basic assumptions. These biases generally fall into two main categories: reporting biases and prescriptions biases. The under reporting of adverse events in spontaneous reporting systems has been well characterized. Certain machine learning-based algorithms have been developed to identify under-reported (or non-reported) adverse events.

Reporting patterns for drugs and adverse events can change over time depending on many factors such as media attention and the popularity of drugs. For example, in 2006 alone, over 18,000 reports were submitted to the FDA for rofecoxib (Vioxx) and heart attack. This large number of reports for heart attack make it appear to signal detection algorithms that heart attacks are more common overall, which increases the expected reporting frequency of heart attack and all other drugs. As a result, another drug that does cause heart attack will have to overcome the higher expected value in order to be detected. In this way, differential reporting patterns cause bias against drugs and adverse events that are reported in large numbers, making it difficult to associate a new drug with a popular event or a rare event to a popular drug.

Prescription bias is another significant source of noise that challenges signal detection algorithms. Prescription bias occurs when treatment choice is not randomized and patient demographics are not matched as is often the case for observational studies. For example, the average age of a patient taking a cholesterol lowering agent is higher than the average age of a randomly selected patient on any given adverse event report. This may cause age-related effects (e.g., a higher risk of heart attack) to be incorrectly associated with cholesterol lowering agents.

Age-related effects may also bias against finding drug-event associations. For example, the average age of a patient that is prescribed amphetamine is typically lower than the average age of a randomly selected patient. In this case, the bias will hide the adverse cardiological effects of amphetamine since it is primarily given to younger patients who have a lower frequency of cardiac events compared to database-wide averages.

Concomitant medications can also bias drug-effect associations. For example, drugs commonly co-prescribed with rofecoxib (Vioxx), the cox 2 inhibitor that was found to increase the risk of stroke and heart attack, are more likely to be associated with heart attack simply because they were commonly taken together. Also, some adverse events are actually caused by the treatment indication rather than the drugs themselves. For example, it is common for diabetes drugs to be reported with hyperglycemia, a symptom of the underlying disease. This causes many false drug-event associations that require human intervention to correct. These biases have gone largely unaddressed in modern signal detection algorithms.

Modifications to signal detection algorithms fall into two main categories: stratification and shrinkage. Stratification is used when other variables (besides the drug and the adverse event) are known or strongly suspected to have an effect on the association. Two examples of such covariates are age and sex. Adverse events that depend on these variables may be easier to detect using stratification. Stratification is a method to amplify signal in the context of known covariates. These methods, however, may only be successful for a few covariates because each division of the data reduces the statistical power in each group. They are further limited because covariates and patient demographic data are not complete in these databases.

Shrinkage methods attempt to reduce the false positive rate by correcting for the bias toward drugs and events with lower numbers of reports. These methods estimate confidence intervals for the unexpectedness statistics and then dampen drug-event signals that have little evidence to support them. These methods are, however, blunt instruments in that, while they do reduce the overall false positive rate, they do not address the underlying issues of bias in the data. Instead, they rely on strong signals to survive the dampening procedure. Addressing the issues of bias more directly yields greater predictive power.

An embodiment of the present invention is based on the observation that the inherent biases in spontaneous reporting systems can be managed using ideas from cohort selection in clinical trial design. In cohort selection, a control individual (or individuals) is selected to match each of the case individuals. The controls are selected based on how well they match a case on pre-defined covariates. This logic can be applied to the adverse event reports: for each drug it is desirable to compare to a control set of reports that match in all covariates except exposure to the drug so that causal inferences can be made. Applying traditional cohort matching techniques directly is, however, limited in at least two ways. Much of the pertinent covariate data on the patients (e.g. age, weight, height, sex, family history, laboratory results, etc) may not be captured by spontaneous reporting systems. Also, even if these data were available, may not be feasible to manually enumerate all the important covariates for each drug and each adverse event combination.

Advantageously, an embodiment of the present invention is a data-driven approach that requires no a priori knowledge of the important covariates but takes advantage of the internal covariances of the data and very large numbers of reports. An embodiment of the present invention uses the covariance between drugs and indications to identify a set of control reports that explicitly matches in concomitant medication use and indication. Described below is evidence that these control cohorts also implicitly match important hidden covariates. Also described are below bootstrapping and statistics that improve the performance of the association analysis.

Latent Signal Detection

The FDA manages a collection of adverse drug event reports to monitor the safety of drugs. They rely on physicians, pharmaceutical companies, and patients to volunteer these reports. Since reporting is not mandatory, many adverse drug events that occur are never reported to the FDA, which has been highlighted as a major limitation of the current system. To address this issue, an embodiment of the present invention uses an algorithm to infer unreported adverse drug events. This embodiment relies on the fact that many adverse events occur together. For example, nausea and vomiting commonly manifest together. Therefore, if a drug is observed to causes nausea, it can be inferred that it also causes vomiting.

A latent signal detection algorithm according to an embodiment of the present invention expands upon this observation in order to detect more subtle associations and identify adverse events that are not reported.

Figure 2:
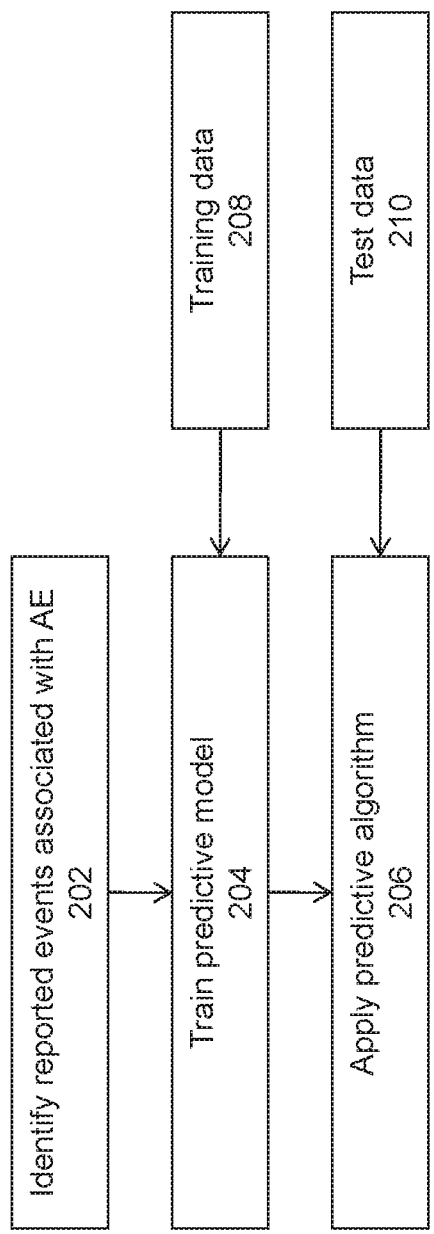
FIG. 2 is a flowchart of a method according to an embodiment of the present invention for latent signal detection.

An embodiment of the present invention provides a method for the latent signal detection as shown in the flowchart of FIG. 2. It should be noted that the described embodiments are illustrative and do not limit the present invention. It should further be noted that the method steps need not be implemented in the order described. Indeed, certain of the described steps do not depend from each other and can be interchanged. For example, as persons skilled in the art will understand, any system configured to implement the method steps, in any order, falls within the scope of the present invention.

As shown in FIG. 2, a method according to an embodiment of the present invention identifies the reported events at step 202 that are associated with a given adverse event. At step 204, a predictive model is trained on the identified events using a training data set 208. At step 206, the predictive algorithm obtained from step 204 is applied to a set of test data 210 so as to infer hidden adverse events.

Figure 3:
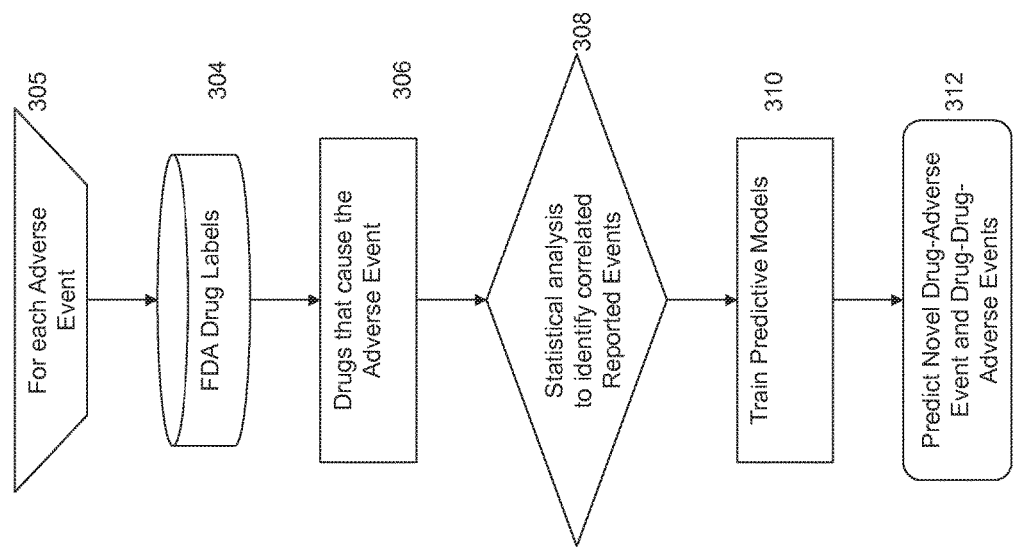
FIG. 3 is a flow diagram of a method according to an embodiment of the present invention for latent signal detection.

Further details of a method for latent signal detection according to an embodiment of the present invention is shown in the flow diagram of FIG. 3. It should be noted that the described embodiments are illustrative and do not limit the present invention. It should further be noted that the method steps need not be implemented in the order described. Indeed, certain of the described steps do not depend from each other and can be interchanged. For example, as persons skilled in the art will understand, any system configured to implement the method steps, in any order, falls within the scope of the present invention.

As shown in FIG. 3, reported events that are associated with the given adverse event are identified at block 302. To do this, the FDA drug labels are applied at step 304 to the reported events. At step 306, those drugs that are known to cause the given adverse event are identified. In an embodiment of the present invention, these are called "positive examples."

A statistical analysis is then used at step 308 to find those reported events that occur most frequently with the positive examples of step 306. In an embodiment, these events are called the "identified events." At step 310, a predictive model is trained using machine learning techniques using the identified events of step 308. In an embodiment, the resulting predictive algorithm is validated using cross validation of the identified positive examples. At step 312, the predictive algorithm is applied to a set of test data to infer hidden adverse events. In an embodiment, the test data is withheld from the previous prior steps. In another embodiment of the present invention, the predictive algorithm is applied at step 212 to the test data and rank the drugs and drug-drug pairs by their likelihood to be associated with the given adverse event.

In a further embodiment of the present invention, a post-processing step is applied to remove drugs or drug-drug pairs that are already known to be associated through known mechanisms. The result is a list of novel drug-adverse event and drug-drug-adverse event predictions.

Statistical Correction of Uncharacterized Bias in Adverse Event Information

Figure 4:
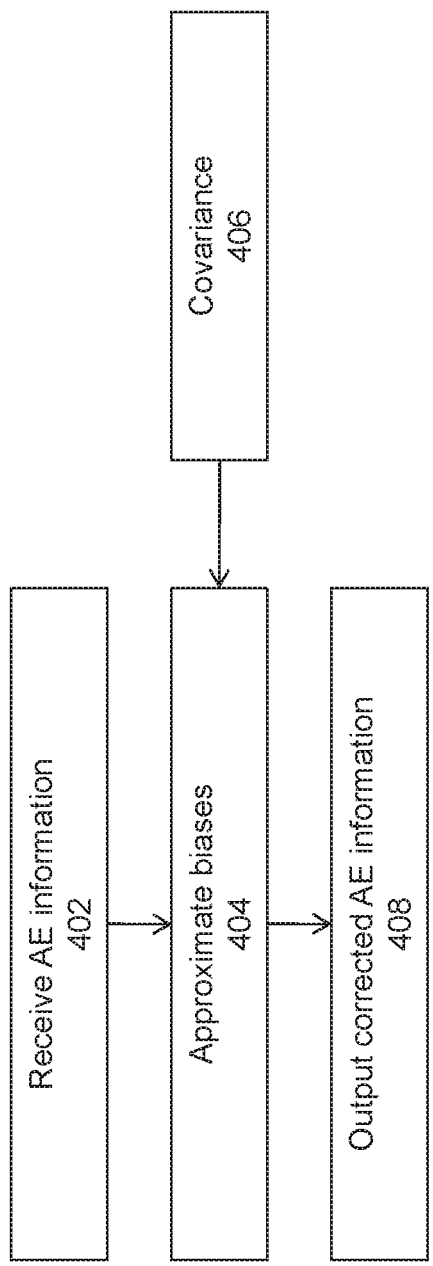
FIG. 4 is a flowchart of a method according to an embodiment of the present invention for statistical correction of uncharacterized bias in adverse event information.

An embodiment of the present invention provides statistical correction of uncharacterized bias in adverse event information as shown in the flowchart of FIG. 4. It should be noted that the described embodiments are illustrative and do not limit the present invention. It should further be noted that the method steps need not be implemented in the order described. Indeed, certain of the described steps do not depend from each other and can be interchanged. For example, as persons skilled in the art will understand, any system configured to implement the method steps, in any order, falls within the scope of the present invention.

The method of FIG. 4 according to an embodiment of the present invention makes use of the above-mentioned AE databases. As noted previously, these large database housed by governmental organizations can be biased, which makes analysis difficult and inference more difficult. In a certain sense, the biases within the information in these databases is "uncorrectable" in that the covariates that may explain them may not be collected in the databases. Such issues have severely limited the utility of traditional statistical methods when applied to these data. Advantageously, an embodiment of the present invention addresses these issues.

A method according to an embodiment of the invention, however, uses covariances in drug co-prescription and co-morbidities to approximate these biases. In an embodiment of the present invention as shown in FIG. 4, adverse event information is received at step 402 such as from the FDA or other databases. At step 404, the biases within such information are approximated using covariances in drug co-prescription and co-morbidities 406. At step 408, corrected adverse event information is output and made available for other analyses.

It has been shown that a method according to an embodiment of the present invention can implicitly correct for the effect of a covariate that is not actually measured as will be described further below. This embodiment of the present invention is a type of automated cohort matching. Statistical methods are disclosed below according to embodiments of the present invention that outperform the traditional methods.

The method of FIG. 4 as an embodiment of the present invention is useful in correcting for noise introduced by concomitant drug use and reporting. As discussed further below, this was shown in an application of the present invention where a "Corrected PRR" score was calculated for each drug-event association and false correlations were examined. This embodiment of the present invention significantly dampened the correlation between concomitant drugs and false association rates. Importantly, these embodiments of the present invention do not simply reduce the association scores without regard to concomitant drug use; in each case where an embodiment of the present invention corrected for the false associations caused by these drugs, it preserved the true drug-event associations. In another application, an embodiment of the present invention corrects for bias introduced by therapeutic indication. Results as discussed further demonstrate that embodiments of the present invention appropriately correct for indication bias and remove correlations stemming from drug-indication associations.

Results

Concomitant drug use is a significant source of noise in the Adverse Event Reporting System. In an embodiment, 1,559 adverse events were identified with very high associations with drugs (PRR>100) on at least 10 reports and which are reported on the FDA drug labels. These represent a set of known strong positive associations. It is hypothesized that other drugs often used concomitantly with these strong association drugs would cause false adverse event associations. As an example, consider the drug pergolide which was taken off the market due to the risk of heart valve damage. Pergolide has a very high association with the heart valve damage adverse event in the AERS (PRR=118.5). In an embodiment, it was shown that drugs used with pergolide also are associated with heart valve damage and that the strength of this association is correlated to the strength of their association with pergolide use ($\rho=0.50$, $p=0.02$). This pattern of association was found repeatedly: the more a drug is reported with a causative drug for an adverse event the more likely that drug is to be falsely associated with the adverse event. This corroborates that concomitant drug use is a significant source of noise in the AERS that must be considered in order to make valid drug-event associations.

A method according to an embodiment of the present invention corrects for noise introduced by concomitant drug use and reporting. This was shown in an application of the present invention where a "Corrected PRR" score was calculated for each drug-event association and false correlations were examined. An embodiment of the present invention significantly dampened the correlation between concomitant drugs and false association rates The investigation of four specific examples is described below. These examples include the examination of rofecoxib and myocardial infarction, isoniazid and hepatic failure, abacavir and rash, and pergolide and heart damage. It was found that in each of these four examples the association scores for the concomitant drugs were significantly adjusted, drastically reducing the false positive rate. Importantly, embodiments of the present invention do not simply reduce the association scores without regard to concomitant drug use; in each case where an embodiment of the present invention corrected for the false associations caused by these drugs, it preserved the true drug-event associations.

Therapeutic indication is a significant source of noise in the Adverse Event Reporting System. The noise introduced by correlations between drug use and therapeutic indication was also investigated. It is a curious observation that many reported adverse events are symptoms of the disease being treated rather than effects of the treatment regimen. For example, it is common to see the adverse event hyperglycemia reported with patients on hypoglycemic agents. This adverse event is most often appropriately attributed to the disease being treated (e.g., Type II Diabetes), rather than the drugs themselves. In an application of an embodiment of the present invention, 658 adverse events were identified that were strongly associated with indications (PRR>100) and with at least 10 reports supporting the association. It was found that drugs reported with these indications were much more likely to be associated with these adverse events—potentially falsely in certain cases. Therapeutic indications are a significant source of bias in the AERS.

Embodiments of the present invention correct for bias introduced by therapeutic indication. Results demonstrate that embodiments of the present invention appropriately correct for indication bias and remove correlations stemming from drug-indication associations. An analysis was performed of four specific examples: hyperglycemia and drugs given to diabetics, elevated cholesterol and cholesterol lowering agents, depression and anti-depressants, arrhythmias and anti-arrhythmics. In each situation, embodiments of the present invention appropriately scale down PRR estimates so that, in general, the drugs are not associated with their indication's side effects. Notably, there are exceptions that may not be false associations. For example, the PRR score between the anti-arrhythmic drug dofetilide and arrhythmias remained high even after correction with embodiments of the present invention. In fact, dofetilide has well established pro-arrhythmic effects which restrict its use. Once again, embodiments of the present invention do not simply dampen all PRR scores without regard to indication. Instead, the scores for drugs associated with indications were found to be reduced significantly more than scores for drugs not associated with these indications.

Embodiments of the present invention correct for clinically significant covariates. In an application of an embodiment of the present invention, 33 adverse events were identified with relatively high average PRR scores and male-oriented sex imbalances. Examples of adverse events that passed these criteria are penile swelling, azoospermia, and cryptorchidism. If sex dependent biases exist in the data, then drugs that are primarily given to males will be more likely to be associated with these male-oriented adverse events. A correlation was observed between male-oriented adverse events and drugs that are mainly prescribed to males, which corroborates the hypothesis here. After an embodiment of the present invention was applied to the data, it was observed that the bias was removed. Notably, the embodiment of the present invention used here was not explicitly trained on sex information. Rather, the embodiment implicitly corrected for the effect of this important covariate.

In addition to correcting for sex-dependent associations, embodiments of the present invention also correct for age-dependent associations. Associations of myocardial infarction were used to demonstrate this. It is noted that older patients are more likely to develop myocardial infarction independent of their treatment exposures, and conversely, younger patients much less likely. Before applying a method according to an embodiment of the present invention, a correlation is found between the average patient age for a drug and the association score to myocardial infarction. Embodiments of the present invention implicitly remove this correlation without any information about age dependencies. This suggests that embodiments of the present invention are corrected for other potentially important covariates implicitly as well. Age and sex were examined because such information is available in the AERS data, and additional covariates are not available.

In an application of an embodiment of the present invention, the results of the association analyses was evaluated against three silver standards: (1) side effects mined from the FDA drug labels, (2) adverse events reported to the FDA after the date used to derive the methods, and (3) the adverse event reports from Canada. Logistic regression was used to evaluate the performance of the uncorrected proportional reporting ratios, "Original PRR," the corrected ratios, "Corrected PRR," and the newly presented association statistic, "T Statistic." It was found that for each of the three silver standards, the T-Statistic performed the best, followed by the Corrected PRR, and the Original PRR performed least well. In fact, the magnitude of the Original PRR score was often inversely proportional to the silver standard, as was the case for both the Future AERS and MedEffect databases. This result implies that examining the top ranked associations based on the Original PRR score will enrich for false positives over true positives.

Estimates of observed and expected reporting frequencies enable alternative signal detection statistics. In order to improve the performance of PRR and enable the use of a more sensitive statistic, the distributions of the observed and expected values were characterized for each drug-adverse event pair with bootstrapping, and confidence intervals were established in the estimates. A t-statistic was used to characterize the difference between the observed and expected values. This statistic has no inherent bias against drugs and events with large numbers of reports. It was found that as the number of reports supporting a known drug-adverse event association increases so does the statistic. While this is an intuitive and expected statistical relationship, the proportionality ratios (e.g. PRR) do not share this characteristic. It was found that the average proportional reporting ratio was inversely proportional to the number of reports for known drug-event associations ($\rho=-0.62$, $p=3.4e-6$), and the T-statistic had a positive relationship with the number of reports for known drug-event associations ($\rho=0.84$, $p<2.2e-16$). Additionally, it was found that the T statistic outperforms PRR at identifying known drug-adverse event associations in all three silver standards.

The increased precision and specificity of embodiments of the present invention enables the construction of databases enumerating off-label effects of drugs. Because the FDA label is based on initial phase 3 trials of limited size, it only has the common adverse events. Many side effects are not listed on the FDA drug label, and resources based on the labels, such as the side effect database (SIDER), may be incomplete. In addition, many side effects may be minor or occur at a low frequency, not warranting a label update. Nevertheless, a more complete compendium of drug effects may be useful in both research and clinical settings.

In an embodiment of the present invention, a database is constructed of 149,527 off-label side effects for 632 drugs and 1,322 adverse events. In an embodiment, the drug-event associations were grouped into five confidence categories according to the amount of supporting evidence in the AERS. The highest confidence category contains 18,137 off-label drug side effects. For comparison, the SIDER database lists 48,577 drug-event associations for 620 drugs and 1,092 adverse events that are also covered by the data mining. A database according to an embodiment of the present invention called OFFSIDES also recovers 41.44% (20,130 drug-event associations) of SIDER from the adverse event reports.

In another embodiment of the present invention, a database of polypharmacy side effects for pairs of drugs is constructed. A particular database that was constructed was called TWOSIDES. As constructed, this database contains 868,221 significant associations between 59,220 pairs of drugs and 1,301 adverse events. These associations are limited to only those that cannot be clearly attributed to either drug alone. The database contains an additional 3,782,910 significant associations for which the drug pair has a higher association score (PRR) than the individual drugs alone. It was found that the TWOSIDES database is enriched for pairs of drugs with known interactions (t=6.6, p=4.9e-11).

In an embodiment, the high confidence associations from OFFSIDES were used to establish class-wide adverse event associations. In an embodiment, 67 significant interactions were identified between ATC drug classes and top level adverse event (COSTART) terms. Twenty-two of these associations are significant multiple hypothesis correction. These results recapitulate common knowledge about the effects of drugs. For example, there is a significant positive association between antiparasitics and nervous systems adverse events.

Drug-effect associations are predictive of shared protein targets. Recent studies have shown two drugs that share similar side effect profiles are more likely to hit the same protein target. This result is replicated using the data mined associations in the OFFSIDES database according to an embodiment of the present invention. A similarity metric was able to significantly predict the number of shared targets between each drug pair in a linear regression model. Two covariates were included in the model: (1) the similarity score as derived using the SIDER database (the FDA drug labels), and (2) the similarity score as derived using the OFFSIDES database. Both variables were significant in a univariate setting ($p<2.2e-16$). Interestingly, it was found that OFFSIDES provided independent information when used in conjunction with the data from SIDER ($F=229.48$, $p<2.2e-16$) as determined by an ANCOVA. A similarity score (ss) cutoff of 2.0 yields precision of approximately 30% in both models and a cutoff of 0.0 corresponds to approximately 18% precision. OFFSIDES compliments SIDER by recovering 100 pairs of drugs (ssOFFSIDES>2) that are known to share targets that SIDER misses (ssSIDER<0). For example, there are 40 known drug targets for fexofenadine and 72 for gabapentin with 26 of those targets shared between them. This many of the same targets suggests that these drugs likely have similar side effect profiles, yet the side effect similarity score based on SIDER is very low (ssSIDER=−0.41). This same pair of drugs, however, has a high side effect similarity score when using the OFFSIDES database (ssOFFSIDES=2.29). Interaction analysis reveals seven clinically significant drug class interactions.

DISCUSSION

Quantitative signal detection in adverse event reporting systems aims to identify and flag significant drug-effect associations from large clinical population databases. However, the utility of these algorithms is limited by well known biases in these data. These biases include under-reporting and prescription biases among others.

In a separate method that addresses under-reporting for the identification of drug-drug interactions. The second source of bias, prescription bias, affects most or all drug oriented observational data bases. This bias occurs when treatment regimens are not randomized or cases and controls are not matched. Physicians will prefer certain drugs in the context of particular covariates. For example, for patients with renal impairment, physicians will often preferentially prescribe moxifloxacin over other fluoroquinolones.

This bias influences adverse event reporting since patients with impaired kidney function will experience specific kidney-related adverse events. Prescription bias is very difficult to remove computationally. Traditional signal detection algorithms typically use the reports for that drug as the "cases" and the rest of the reports in the database as the "controls." The cases can be very biased in patient conditions and demographics.

The methods according to embodiments of the present invention essentially identify a matched set of controls by using all available data to define and correct for the key correlated variable values. The methods according to embodiments of the present invention explicitly remove two major sources of bias: concomitant medication use and prescription indication. The methods according to embodiments of the present invention also implicitly remove other biases, such as patient demographic and condition.

A method according to an embodiment of the present invention for correction of bias and producing more appropriate estimates of the expected reporting proportions between drugs and adverse events complements other signal detection methods. In fact, the various methods can be used together seamlessly. The methods according to embodiments of the present invention provide a pre-processing step that is applied to the data before traditional analysis is performed. In addition, the relative effect of methods according to embodiments of the present invention can be controlled through parameters that allow the user to adjust the stringency with which the method is applied. This enables the methods of the present invention to be used in a wide variety of applications.

It should be noted that certain embodiments of the present invention may not completely remove all of the biases in the data. In such embodiments, likely false association signals are more likely to be reduced, while those that are likely true positive are either not changed or are amplified (as in the case of amphetamine). Also, because certain embodiments of the present invention adjust the expected values to match the anticipated bias in the observed values, such embodiment may dampen the signal of true associations in the cases where the bias is large. In certain embodiments, the ability to remove the false associations introduced by treatment indications can be hampered by the imperfect availability of indication data.

While adverse event reports tend to list drugs a patient is taking, the reporting of indications is less reliable. As a result, the adverse events reported may be attributable to one of the indications. Methods that impute the indications based on the medications present on the report may help mitigate this limitation.

It should also be noted that certain embodiments of the present invention may be more computationally expensive than the basic proportionality statistics because embodiments of the present invention calculate two large covariance matrices. In such embodiments, however, such computations are only performed once for each version of the database analyzed.

Materials and Data Sources

In an application of the present invention, 1,851,171 adverse event reports were downloaded from the Adverse Event Reporting System from the Food and Drug Administration's website from the first quarter of 2004 through the first quarter of 2009. In addition, the Side Effect Resource (SIDER) was downloaded. SIDER is a database of the drugs, adverse events, and indications mined from the FDA drug labels and Canada's MedEffect resource, the sister database to the Adverse Event Reporting System containing approximately 300,000 adverse event reports (downloaded September 2009). For comparison drug-target information was downloaded for use correlating side-effect similarity to shared drug targets. Also, an independent database was downloaded for the adverse event reports for third quarter 2009 to fourth quarter 2010 for validation purposes.

Statistical Model and Assumptions

Embodiments of the present invention may apply two assumptions. It is assumed that the observed reporting frequency between any drug and event (say drug x and event y) is a biased estimate of the incidence. The incidence being defined as the actual proportion of patients on drug x that experienced event y (given that they had any adverse events at all). It is also assumed that an adverse event (e.g., event y) on any given report can be attributed to the drug of interest (e.g., drug x), the other drugs on the report, or the indications for which the drugs are given.

Signal detection algorithms identify drug-adverse event pairs that are disproportionately represented in the data for follow up analysis. Most of these algorithms derive statistics from a contingency table for each given drug-adverse event pair. The algorithms then compute the ratio of the observed-to-expected number of reports for a given drug-adverse event pair:

$$\frac{obs}{exp} = \frac{a(a+b+c+d)}{(a+b)(a+c)}.$$

This ratio has taken on different disproportionality forms, such as the proportional reporting ratio (PRR) and the reporting odds ratio (ROR):

$$PRR = \frac{a/(a+b)}{c/(c+d)}$$

$$ROR = \frac{a/b}{c/d}$$

These statistics, and other similar methods, are approximately equivalent since b is much larger than a, and d is much larger than c. These ratios are generally referenced as $$\frac{E[O_{xy}]}{E[E_{xy}]}.$$

An assumption in an embodiment of the present invention is that, under the null hypothesis, both $O_{xy}$ and $E_{xy}$ are biased estimators of the actual incidence, $I_{xy}$. This ratio can be written as follows:

$$\frac{I_{xy} + \epsilon}{I_{xy} + \beta},$$

where $\beta$ is the bias of $E_{xy}$ and $\epsilon$ is the bias in $O_{xy}$. Note that under the null hypothesis $$\lim_{\beta \to \epsilon} = \frac{I_{xy} + \epsilon}{I_{xy} + \beta} = 1.$$

The bias cannot be computed directly. Therefore, an applied strategy is to adjust the cohort of reports upon which the estimate, E, is based so that $\beta$ approaches $\epsilon$. This approach is similar to those employed by cohort matching methods where each case patient is matched to control patients that are similar in a set of predefined covariates. Similarly, a goal of this embodiment is to find a matched control cohort of reports that more closely matches the case reports (e.g., have the same or similar biases).

In an embodiment, these control reports were used to produce a more realistic estimate of the expected value given the biases in the case cohort. To identify the set of control reports to use, the second basic assumption is applied.

Previous work has identified different types of bias in spontaneous reporting systems. These include concomitant drug use, indication co-morbidities, selective reporting, and prescription biases. Embodiments of the present invention, however, address concomitant drug use and indication co-morbidities explicitly and the other forms of bias implicitly.

Concomitant drug use can cause drugs which are commonly taken together to be incorrectly associated with each other's side effects. For each drug, an embodiment of the present invention identifies other drugs that are significantly co-reported and perform an analogous identification of co-reported indications. This yields two sets of control reports (one set for co-reported drugs and one for co-reported indications). An embodiment of the present invention restricts the cohort of reports upon which the expected estimate, E, is based to the union of these two sets. It is beloved that an estimator that uses only these reports will have more similar biases (e.g., will be a better control cohort) than an estimator that uses the entire database of reports.

More explicitly for an embodiment of the present invention, let x be the drug of interest, let R be the set of all adverse event reports, and let $D_{all}$ be the set of all drugs. The matched cohort of reports, M, is defined as follows: $M=R_i$: $D_{Ri}D_x \neq \forall R_i R$ where $R_i$ is report i, $D_{Ri}$ is the set of drugs listed on $R_i$, and $D_x$ is the set of drugs that are correlated in reporting with x and is defined as $D_x = d_i : \phi_{x,d_i} > c_x \forall d_i D_{all}$. Where $\phi$ is Pearson's phi coefficient. Note that $c_x$ is a parameter that requires optimization and is dependent on x. This parameter controls the relative size of the background, or control, set of reports to the number of reports for drug x (e.g., the foreground or cases).

The same value for $c_x$ cannot be used for all drugs since some drugs are tightly co-reported with many other drugs and others with only a few. This would result in different relative background sizes. To keep the size of the background relatively constant, the value of $c_x$ was independently determined for each drug. This was done by first setting $c_x$ to 1.0 and determining the size of the background. If the number of reports in the background was less than a predefined value, the value was relaxed by dividing by 1+n, where n is the number of iterations already performed. For example, for the first iteration, n=0 so $c_x=1/(1+0)=1.0$. For the second iteration n=1 so $c_x=1/(1+1)=0.5$, the third, $c_x=1/(1+2)=0.333$, and so on.

This was done in an embodiment until the size of the background was greater than or equal to the desired size. To explore the relationship between the ratio of the background to the foreground in an embodiment, four distinct runs (A, B, C, and D) were performed. In A, the reporting correlation cutoff was relaxed so that the background was, on average, 10 times the size of the foreground. In B, the average was required to be 20 times the size of the foreground, and 150 times for C. For D, no restriction was placed and the entire database was used as the background (the average was 800 times the foreground).

It is noted that no unbiased gold standard for adverse drug events exists. The drug-event associations from the FDA drug labels are an option for comparison. But it is important to note that the labels are biased toward the more common adverse events that are observed and reported in pre-marketing clinical trials. This bias will limit the applicability of the drug labels since the goal of proportionality analysis, in this context, is to identify rare and unexpected side effects of drugs. An independent adverse event database, such as Canada's MedEffect database, can also be used for evaluation. Since such a database will suffer from the same types of confounding variables, it is necessary to take only a subset of high confidence associations.

In an embodiment, only those associations where there was only one drug listed on the report were extracted under the assumption that if only one drug is listed then it is the causative agent. Similarly, a subset of AERS (Quarter 3 2009 through Quarter 4 2010) was used in this embodiment that was not used in the original analysis as a third silver standard. Again, only those reports that list exactly one drug were used so as to mitigate confounding effects.

In an application of an embodiment of the present invention a statistical analysis of eight case studies was performed. To demonstrate how a method according to an embodiment of the present invention corrects for likely false associations, four drugs and four indications were manually selected that exemplify a method according to an embodiment of the present invention. Drugs were chosen which are notably associated with severe side effects. These drugs-side effect pairs were refecoxib and heart attacks, isoniazid and hepatic failure, pergolide and heart valve damage, and abacavir and rash. Other drugs that are concomitantly taken with these four drugs are at risk of being incorrectly associated with these side effects simply through correlation in reporting. The associations between the concomitant drugs and the four adverse events are termed "likely false." The FDA drug labels were then used to define known true associations between drugs and the four adverse events.

In correct operation, the method according to an embodiment of the present invention the signal for the "likely false" associations will be dampened to a greater degree than that of known true signals. Test for a difference in the log ratio of the original to corrected association scores was then performed. The log ratio was used so that the data conforms to the assumptions of the statistical test (Student's T-Test) and is uncorrelated with the magnitude of the association score. This analysis was repeated for four indications.

Drugs that are significantly reported with these indications are more likely to be falsely associated with the indications effects. These associations are termed "likely false." A set of known true associations from the FDA drug labels was defined and the statistical analysis was repeated.

In an application of an embodiment of the present invention bootstrapping and using the Student's T statistic to evaluate drug-event associations was then performed. The disproportionality analysis statistics, such as the proportional reporting ratio, are biased toward drugs and events with smaller numbers of total reports. This makes it more difficult to associate "popular" drugs with rare adverse events and "popular" events with rare drugs. As the number of reports for a given drug increase the average proportional reporting ratio between that drug and its known side effects decreases ($\rho=-0.62$, $p=3.4e-6$).

Alternatively, bootstrapping can be used to estimate the mean and variance of the proportion of reports associating a given drug and adverse event. This enables the use of statistics, like the Student's T Statistic, that represent a more sensitive way to associate drugs with adverse events. In this case, the difference between the observed and expected values is tested rather than the ratio. In contrast, the pro-portional reporting ratio, the T statistic between drugs and their known side effects, increases as the number of reports increases ($\rho=0.84$, $p<2.2e-16$). This characteristic makes the T statistic a more desirable statistic when identifying more common effects or rare effects for common drugs. It also makes the T statistic significantly more predictive of the associations reported in all three silver standards.

In an embodiment, drug side effect similarities were used to predict shared targets. Previous work has shown that a drug's side effects can be used to predict protein targets. Other investigations have shown that if two drugs are similar in the side effects they elicit, then they are more likely to share a common drug target. As validation of the biological relevance of the methods according to embodiments of the present invention, this result was replicated the above-described mined associations. The similarity between two drugs was calculated by computing the Tanimoto coefficient between the drug's adverse event bit vectors (in these adverse event bit vectors each bit represents one adverse event and is set if the drug has a significant association with the adverse event). Some drugs have higher similarity scores on average using this metric, so a z-score normalization by drug was performed. These "z-similarities" were calculated for both the SIDER data set (the side effects extracted from the FDA drug labels) as well as for the OFFSIDES dataset according to an embodiment of the present invention. The similarity score's ability to predict the number of targets two drugs share was tested using a multivariate linear regression and tested for independence between SIDER and OFF-SIDES using an F test (ANCOVA).

An embodiment of the present invention provides a generalization of the method for multi-item associations (drug-drug interactions). The analysis used for single drug-event associations for drug-drug-event associations was repeated. In this case, as in the single-item associations, the correlation cutoff was relaxed until the desired background to foreground ratio was met. In this embodiment, a report can be included in the background by being correlated with either drug in the pair individually (and not necessarily with both drugs together). As before, the proportionality statistics calculated and confidence intervals were estimated by boot-strapping. These putative drug interactions were evaluated against a list of critical or significant interactions maintained by the Veterans Association hospital.

The OFFSIDES database as an embodiment of the present invention was constructed as a union of runs B and C. In run B, the background-to-foreground ratio is tighter where associations between drugs and events are held to a more stringent background. Significant associations from run B is of higher confidence than C. Four confidence categories (1-4) were established with a confidence level of 4 indicating the highest confidence and a confidence level of 1 the lowest confidence. It should be noted, however, that all associations reported in OFFSIDES according to an embodiment of the present invention are statistically significant. Confidence level 4 indicates that the p-value was in the top 10% of associations in run B. Confidence level 3 indicates that the p value was in the top 25% of associations in run B or the top 5% from run C (excluding any associations also in category 4). Confidence level 2 indicates that the association was found to be statistically significant (p<0.05) in run B and in the top 50% of the p-values in run C. The same confidence categories were used in the creation of the polypharmacy side effect database (OFF-BOTH-SIDES) according to an embodiment of the present invention. The drug-drug-event associations reported are filtered for only those associations not easily explained by either drug alone. Any drug-drug-event associations were removed that were a known to be caused by at least one of the two associated drugs according the FDA drug labels. In addition, any associations were removed where the association score for one of the single drugs is greater than the associations score for both drugs (e.g., if $PRR_{x,y,e} < PRR_{x,e}$ or $PRR_{x,y,e} < PRR_{y,e}$, where x and y are the drugs and e is the event).

It should be appreciated by those skilled in the art that the specific embodiments disclosed above may be readily utilized as a basis for modifying or designing other image processing algorithms or systems. It should also be appreciated by those skilled in the art that such modifications do not depart from the scope of the invention as set forth in the appended claims.

What is claimed is:

1. A computer-implemented method for detection of latent signals in adverse event information, comprising:
   receiving a set of adverse event information comprising information for a plurality of adverse events, wherein the information comprises a first characteristic and a second characteristic for each adverse event of the plurality of events;
   identifying covariances for the first and second characteristics of the plurality of adverse events;
   correcting the set of adverse event information based on the identified covariances in order to correct for a third characteristic of the plurality of adverse events that is not included in the information;
   identifying a first adverse event from the plurality of adverse events;
   identifying, from the corrected set of adverse event information, a set of adverse events from the plurality of adverse events that are associated with the first adverse event;
   training a predictive model, using the identified set of adverse events and a training dataset, to predict hidden adverse events that are related to the identified set of adverse events and not associated with the first adverse event; and
   applying the predictive model to a test dataset to identify a set of hidden adverse events to be associated with the first adverse event.

2. The method of claim 1 further comprising validating the trained predictive model prior to applying the trained predictive model to the test dataset.

3. The method of claim 1, wherein identifying the set of adverse events comprises:
   identifying a set of drugs known to cause the first adverse event; and
   performing a statistical analysis to identify adverse events associated with the set of drugs from the set of adverse event information.

4. The method of claim 3, wherein identifying the set of drugs comprises analyzing drug labels to identify the set of drugs.

5. The method of claim 1, wherein applying the predictive model to a test dataset to identify a set of hidden adverse events comprises processing results of the applied predictive model to remove adverse events already associated with the first adverse event.

6. The method of claim 1 further comprising validating the predictive model using cross validation of the set of adverse events.

7. The method of claim 1, wherein the test dataset is not included in the training dataset.

8. The method of claim 1, wherein applying the predictive model to a test dataset to identify a set of hidden adverse events comprises ranking the hidden adverse events of the set of hidden adverse events according to a likelihood of association with the first adverse event.

9. The method of claim 1, wherein identifying covariances comprises identifying covariances in drug co-prescription and co-morbidities.

10. The method of claim 1, wherein the first characteristic is a prescribed drug and the second characteristic is an indication.

11. A non-transitory computer-readable medium including instructions that, when executed by a processing unit, cause the processing unit to detect latent signals in adverse event information, by performing the steps of:
    receiving a set of adverse event information comprising information for a plurality of adverse events, wherein the information comprises a first characteristic and a second characteristic for each adverse event of the plurality of events;
    identifying covariances for the first and second characteristics of the plurality of adverse events;
    correcting the set of adverse event information based on the identified covariances in order to correct for a third characteristic of the plurality of adverse events that is not included in the information;
    identifying a first adverse event from the plurality of adverse events;
    identifying, from the corrected set of adverse event information, a set of adverse events from the plurality of adverse events that are associated with the first adverse event;
    training a predictive model, using the identified set of adverse events and a training dataset, to predict hidden adverse events that are related to the identified set of adverse events and not associated with the first adverse event; and
    applying the predictive model to a test dataset to identify a set of hidden adverse events to be associated with the first adverse event.

12. The non-transitory computer-readable medium of claim 11, wherein the processor further performs a step for validating the trained predictive model prior to applying the trained predictive model to the test dataset.

13. The non-transitory computer-readable medium of claim 11, wherein identifying the set of adverse events comprises:
    identifying a set of drugs known to cause the first adverse event; and performing a statistical analysis to identify adverse events associated with the set of drugs from the set of adverse event information.

14. The non-transitory computer-readable medium of claim 13, wherein performing the statistical analysis comprises analyzing drug labels of the set of drugs.

15. The non-transitory computer-readable medium of claim 11, wherein applying the predictive model to a test dataset to identify a set of hidden adverse events comprises processing results of the applied predictive model to remove adverse events already associated with the first adverse event from the results.

16. The non-transitory computer-readable medium of claim 11, wherein the instructions further cause the processor to perform the step of validating the predictive model using cross validation of the set of adverse events.

17. The non-transitory computer-readable medium of claim 11, wherein the test dataset is not included in the training dataset.

18. The non-transitory computer-readable medium of claim 11, wherein applying the predictive model to a test dataset to identify a set of hidden adverse events comprises ranking the hidden adverse events of the set of hidden adverse events according to a likelihood of association with the first adverse event.

19. The non-transitory computer-readable medium of claim 11, wherein identifying covariances comprises identifying covariances in drug co-prescription and co-morbidities.

20. The non-transitory computer-readable medium of claim 11, wherein the first characteristic is a prescribed drug and the second characteristic is an indication.

* * * * *